(12) United States Patent
Nason et al.

(10) Patent No.: US 8,932,230 B2
(45) Date of Patent: Jan. 13, 2015

(54) CONTROLLING FLOW OF EXHALED BREATH DURING ANALYSIS

(75) Inventors: Kevin Nason, Menlo Park, CA (US); Jonathan Fay, San Mateo, CA (US); Bryan P. Flaherty, Half Moon Bay, CA (US); Bhairavi R. Parikh, Palo Alto, CA (US)

(73) Assignee: Aerocrine AB, Solna (SE)

( * ) Notice: Subject to any disclaimer, the term of this patent is extended or adjusted under 35 U.S.C. 154(b) by 2556 days.

(21) Appl. No.: 11/348,943

(22) Filed: Feb. 6, 2006

(65) Prior Publication Data

US 2006/0195040 A1 Aug. 31, 2006

Related U.S. Application Data

(63) Continuation-in-part of application No. 11/053,047, filed on Feb. 7, 2005, now abandoned.

(51) Int. Cl.
*A61B 5/08* (2006.01)
*G01N 33/497* (2006.01)

(52) U.S. Cl.
CPC .............. *G01N 33/497* (2013.01); *A61B 5/082* (2013.01); *A61B 5/0803* (2013.01)
USPC .......................................... 600/532; 600/529

(58) Field of Classification Search
USPC ................................................ 600/529–543
See application file for complete search history.

(56) References Cited

U.S. PATENT DOCUMENTS

| | | | | |
|---|---|---|---|---|
| 4,202,352 A | * | 5/1980 | Osborn | 600/532 |
| 4,248,245 A | | 2/1981 | Kempin | |
| 4,297,871 A | * | 11/1981 | Wright et al. | 73/23.3 |
| 4,476,708 A | * | 10/1984 | Baker et al. | 73/23.3 |
| 5,092,326 A | * | 3/1992 | Winn et al. | 128/205.13 |
| 5,129,401 A | * | 7/1992 | Corenman et al. | 600/529 |
| 5,321,972 A | | 6/1994 | Stock | |
| 5,739,412 A | | 4/1998 | Stock et al. | |
| 5,795,187 A | | 8/1998 | Sipe | |
| 5,873,361 A | | 2/1999 | Hakala | |
| 6,010,459 A | | 1/2000 | Silkoff et al. | |
| 6,041,777 A | * | 3/2000 | Faithfull et al. | 128/200.24 |
| 6,067,983 A | | 5/2000 | Stenzler | |
| 6,616,896 B2 | * | 9/2003 | Apperson et al. | 422/84 |
| 6,733,463 B2 | | 5/2004 | Moilanen et al. | |
| 6,815,211 B1 | | 11/2004 | Blazewicz et al. | |
| 7,435,225 B2 | * | 10/2008 | Hietala | 600/532 |
| 2003/0050567 A1 | * | 3/2003 | Baghdassarian | 600/532 |
| 2004/0017570 A1 | * | 1/2004 | Parikh et al. | 356/437 |
| 2005/0053549 A1 | | 3/2005 | Parikh et al. | |

(Continued)

FOREIGN PATENT DOCUMENTS

| | | |
|---|---|---|
| DE | 19545794 A1 | 6/1997 |
| DE | 19619763 A1 | 11/1997 |
| EP | 1505389 A1 | 2/2005 |

(Continued)

*Primary Examiner* — Michael Kahelin
*Assistant Examiner* — Karen Toth
(74) *Attorney, Agent, or Firm* — Renner, Otto, Boisselle & Sklar, LLP

(57) ABSTRACT

The flow rate of a gaseous sample of exhaled breath through an analytical device is controlled by a pump, and in certain embodiments two pumps. Placement of the analyte sensor in a secondary stream branching off of the primary stream through the device offers further control over the manner, duration, and quantity of the breath that is placed in contact with the sensor.

15 Claims, 3 Drawing Sheets

(56) References Cited

U.S. PATENT DOCUMENTS

2005/0083527 A1 4/2005 Flaherty et al.
2006/0241507 A1* 10/2006 Carlson et al. ................ 600/532

FOREIGN PATENT DOCUMENTS

| WO | WO 02/091921 A1 | 11/2002 |
| WO | WO 2004/010120 A1 | 1/2004 |

* cited by examiner

CONTROLLING FLOW OF EXHALED BREATH DURING ANALYSIS

CROSS REFERENCE TO RELATED APPLICATION

This is a continuation-in-part of co-pending U.S. patent application Ser. No. 11/053,047, filed Feb. 7, 2005, the contents of which are hereby incorporated herein by reference.

BACKGROUND OF THE INVENTION

1. Field of the Invention

This invention resides in the field of systems and methods for the analysis of exhaled breath.

2. Description of the Prior Art

Analyses of exhaled breath from human subjects are of value in many applications, including the diagnosis and management of several physiological conditions. A change in the nitric oxide (NO) concentration in the exhaled breath of a person suffering from asthma, for example, can indicate a change in the level of inflammation in the airway of the person, which in turn can indicate an increase in the likelihood of an asthma attack. Another component of exhaled breath whose concentration can be correlated with a physiological abnormality is carbon monoxide, a rise in which can be an early indication of the onset of hemolytic jaundice. A still further example is hydrogen, whose rise can indicate malabsorption of carbohydrate. These gases are typically present in trace amounts, notably at concentrations in the parts per billion (ppb) range, and concentration changes that are still within trace amounts can indicate abnormalities before they can be detected at the parts per million range.

The utility and reliability of an analyzer for exhaled breath are limited by fluctuations in temperature, humidity, and breath flow, any of which can interfere with and influence the analytical result. Interference due to these factors is especially acute when the analyzer is used for measuring trace amounts of the analyte. Thus, any device that seeks to quantify analytes in trace amounts in exhaled breath must minimize the effect of these factors or compensate for their presence.

Among these factors, the one that is the most difficult to control in most cases is the flow rate of the exhaled breath of the subject through the analytical device. A crude method in the prior art for controlling the breath flow rate is a verbal instruction from the clinician performing the analysis to the subject, calling for the subject to breathe out faster or slower to correct deviations from the design rate for the analyzer. This method is limited by the subject's ability to adjust the flow rate, particularly when the subject is a child, and is generally impractical for trace gas analyses over a wide range of concentration. An alternative is to include a variable flow resistance in the analyzer and altering the resistance to correct for the deviations. A device that incorporates this capability is disclosed in Moilanen, E., et al., U.S. Pat. No. 6,733,463 B1, issued May 11, 2004. The device in the Moilanen et al. patent contains a mechanical, electrically controlled throttle that is controlled by a signal from a mass flow meter inside the device. Unfortunately, the Moilanen et al. device is complex, requiring multiple components under feedback control.

SUMMARY OF THE INVENTION

The present invention resides in apparatus for exhaled breath analysis that includes a housing constructed to receive exhaled breath directly from a subject, a flow-through passage within the housing for the travel of the exhaled breath, an analyte sensing element in the flow-through passage, and a pump or pump system to control the rate at which the subject exhales into the housing and to cause the exhaled breath to flow through the passage at a controlled rate. The invention can be used for the analysis of a variety of gaseous analytes, including those in trace amounts, and is of particular interest the quantification of NO.

DETAILED DESCRIPTION OF THE INVENTION AND PREFERRED EMBODIMENTS

While the invention is susceptible to a variety of constructions, the features defining the invention and its novelty are best understood by a detailed review of specific embodiments. Three such embodiments are shown in the Figures and described below.

Figure 1:
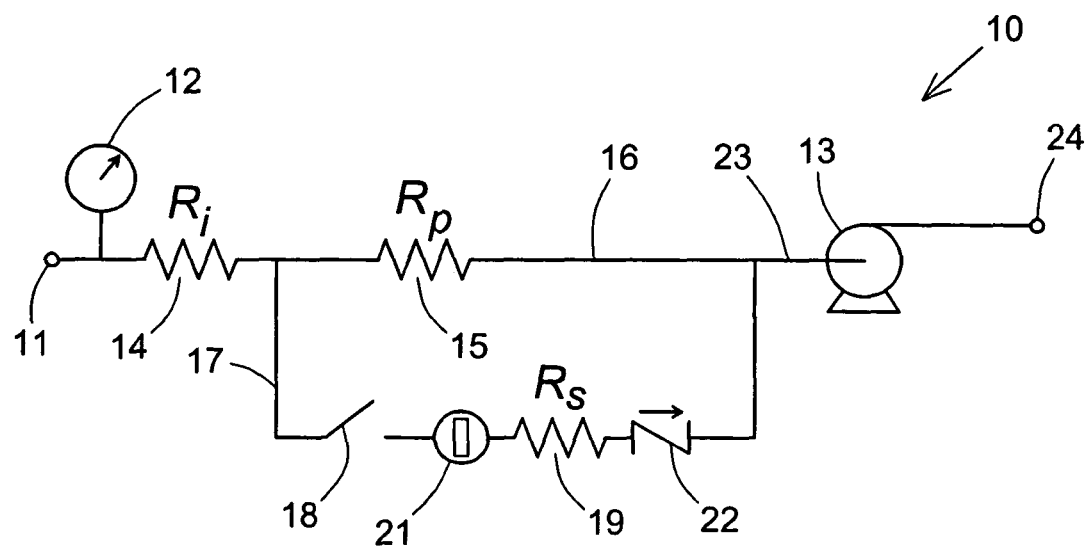
FIG. 1 is a diagram of the components of an analytical device embodying the features of the present invention.

FIG. 1 represents a network 10 of components that constitute the functional parts of an analytical device in accordance with the invention. The device itself can be a mask or similar device that can be worn by, or otherwise mounted to, the user, either directly or through a mouthpiece, in a manner that will capture the breath exhaled by the user. Exhaled breath enters the device at an inlet 11. The pressure of the exhaled breath is detected by a pressure sensor 12 in the device with an operating range appropriate to the anticipated range of breath pressure. In one embodiment, this range is 5 to 20 cm of water (approximately 0.45 to 1.8 psig), the lower limit of this range being the pressure necessary to close the velum of the typical user and the upper limit a pressure at which the typical user will feel discomfort. The pump 13 can operate in various ways. For example, when the pressure detected by the sensor rises to a threshold value, which may be the lower limit of the above range, the pump 13 can be actuated by a signal from the pressure sensor, and as exhalation into the device continues and the pressure eventually drops below the lower limit, the pump can be de-actuated (turned off). One example of a suitable pump is Model No. UNMP50 of KNF Neuberger, Inc., Trenton, N.J., USA. This pump has a free-flow capacity of 66.7 cm$^3$/s, a maximum vacuum of 400 mbar (63 cm H$_2$O), and a maximum continuous pressure of 0.5 bar (79 cm H$_2$O). The pump is preferably sufficiently resistant to inlet pressure to maintain a substantially constant flow rate despite changes in the subject's mouth pressure across the range of interest. In an alternative design, the pump can be equipped with closed-loop control using the pressure sensor 12 for feedback.

An optional component in the flow path of the breath through the device is a flow resistor 14 which in this embodiment is positioned downstream of the pressure sensor 12 and upstream of the pump 13. In certain embodiments of the invention, a second flow resistor 15 is included in the flow path as well, downstream of the first resistor 14 but still upstream of the pump 13. The flow resistor or resistors will assist in limiting the flow to a desired flow rate, which may for example be 50 cm$^3$/s, and in increasing the pressure in the user's mouth, throat, or air passages. One example of a flow resistor is a fixed orifice in the form of a round aperture having a diameter of approximately 0.11 cm. Flow resistors of other types will be readily apparent to those skilled in the art and can be used in place of an orifice. Flow resistors can serve to tune the system to the specifications of the pump 13.

The first resistor offers a resistance which will be designated herein by the symbol $R_i$. The flow path downstream of the first resistor 14 in this embodiment is divided into two streams—a main stream 16 and a side stream 17. These streams will also be referred to herein as a primary stream and a secondary stream, respectively. The second resistor 15 resides in the main stream 16 and offers a resistance which will be designated here by the symbol $R_p$, which can be variable or fixed. Examples of variable resistors are motor-controlled needle valves, solenoid-controlled needle valves, manual needle valves, and pinch-tube valves, all of which also offer resistance to the flow. An example of a fixed resistor is a non-variable orifice. Included in the side stream 17 is a side stream valve 18, which is preferably a shut-off, i.e., open/close, valve and a resistor 19 to allow flow into or prevent flow from entering the side stream, and to thereby control the flow distribution between the two streams. An example of a shut-off valve suitable for this application is a solenoid valve; other examples will be readily apparent to those skilled in the art. After a selected period of time from the start of the exhale, the side stream valve 18 can be opened to allow breath flow to occur in parallel through the main and side streams. The valve may for example be set to open at 7 seconds after the start of exhalation flow into the device, and to remain open until 10 seconds after the start of exhalation flow. Under this protocol, all exhaled breath will pass through the main stream 16 for the first seven seconds of the test, then through both the main and side streams 16, 17 for the next three seconds.

The side stream 17 contains an analyte sensor 21 that detects the level of the analyte (NO or otherwise) in the exhaled breath passing through the side stream. The analyte sensor 21 may also offer flow resistance and eliminate the need for a separate side stream resistor 19. In the representation of such an embodiment in FIG. 1, the side stream resistor 19 is incorporated into the analyte sensor 21. The side stream valve 18 can also serve to provide the flow resistance in the side stream, and accordingly the side stream resistor 19 can be incorporated into the valve 18. In general, flow resistance in the side stream is designated herein by the symbol $R_s$. Optionally, the side stream can contain other components, such as a carbon dioxide scrubber (not shown). A check valve 22 is included in the side stream to prevent backflow.

A constant flow rate of exhaled breath through the device 10 can be maintained in any of several ways. One way is to use a main stream resistor 15 whose resistance $R_p$ is variable while the side stream resistor 19 has a non-variable resistance $R_s$. The main stream resistor may have a value of $R_{p1}$ when the side stream valve 18 is closed, and be programmed or set to change to a value of $R_{p2}$ when the side stream valve 18 is open. The values of $R_{p1}$ and $R_{p2}$ can be chosen so that the sum of the flow rates through the main stream 16 and the side stream 17 when the side stream valve 18 is open will equal the flow rate through the main stream 16 when the side stream valve 18 is closed. The choice of resistance levels for $R_{p1}$ and $R_{p2}$ may be influenced in part by the resistance from other components in the flow stream, such as the other resistors, valves, and sensors, as well as the voltage and capacity of the pump.

In the embodiment shown in FIG. 1, the main stream 16 and side stream 17 recombine into a single passage 23 upstream of the device outlet 24. Since the pump 13 is positioned downstream of the point where the main stream 16 and side stream 17 recombine, the pump 13 controls the overall flow of the system rather than each stream individually. The placing of the pump 13 downstream of the sensor 12 also avoids the risk of contaminating the sensor with the pump effluent.

One example of a set of values for the pump pressure drop, the flow rate through the device as a whole, and the various resistances for a flow rate of 50 cm$^3$/s through the device is listed in Table I below. In this example, the resistance in the main stream $R_p$ is variable while the remaining resistances $R_i$ and $R_s$ are constant. The symbols used in Table I and the succeeding tables are as follows:

$\Delta P$ denotes the pressure drop across the pump 13.

$R_i$ denotes the resistance offered by the first (upstream) resistor 14.

$R_p$ denotes the resistance offered by the main stream resistor 15.

$R_s$ denotes the resistance offered by the side stream components 19, 21, and 22.

V denotes the total flow rate of exhaled breath through the device.

TABLE I

Example 1: Operating Parameters

| Parameter | Side Stream Valve 18 Closed | Side Stream Valve 18 Open |
|---|---|---|
| $\Delta P$ | 32 cm $H_2O$ | 32 cm $H_2O$ |
| $R_i$ | 0.4 cm $H_2O$/cm$^3$/s | 0.4 cm $H_2O$/cm3/s |
| $R_p$ | 0.24 cm $H_2O$/cm$^3$/s ($R_{p1}$) | 0.29 cm $H_2O$/cm$^3$/s ($R_{p2}$) |
| $R_s$ | (infinite) | 1.5 cm $H_2O$/cm$^3$/s |
| V | 50 cm$^3$/s | 50 cm$^3$/s |

In the example above, the two values of $R_p$ ($R_{p1}$ and $R_{p2}$) are chosen to maintain a constant flow rate of 50 cm$^3$/s throughout the test, with a flow rate of 8 cm$^3$/s through the analyte sensor 21, i.e., a main stream to side stream flow ratio of 42:8, when the side stream valve is open. To achieve this flow ratio, the ratio of $R_{p2}$ to $R_s$ will be 8/42=0.29, and to assure that the same flow rate will occur when the side stream valve is closed, the ratio of $R_{p1}$ to $R_{p2}$ is 42/50=0.84. Thus, when the side stream 17 is open during the final three seconds of exhalation, breath will flow through the side stream at a rate of 8 cm$^3$/s, while the remainder will flow at 42 cm$^3$/s through the main stream 16.

In a second example, the resistance from all resistors remains constant while the pump flow rate is varied. This configuration utilizes a variation in the pressure drop across the pump to compensate for the change in the overall flow path resistance that occurs when the side stream is opened. The ratio of the resistance $R_p$ at the main resistor 15 and the resistance $R_s$ at the side stream resistor 19 is again 8/42=0.29, as in Example 1.

TABLE II

Example 2: Operating Parameters

| Parameter | Side Stream Valve 18 Closed | Side Stream Valve 18 Open |
|---|---|---|
| $\Delta P$ | 34.3 cm $H_2O$ | 32 cm $H_2O$ |
| $R_i$ | 0.4 cm $H_2O$/cm$^3$/s | 0.4 cm $H_2O$/cm$^3$/s |
| $R_p$ | 0.29 cm $H_2O$/cm$^3$/s | 0.29 cm $H_2O$/cm$^3$/s |
| $R_s$ | (infinite) | 1.5 cm $H_2O$/cm$^3$/s |
| V | 50 cm$^3$/s | 50 cm$^3$/s |

Figure 2:
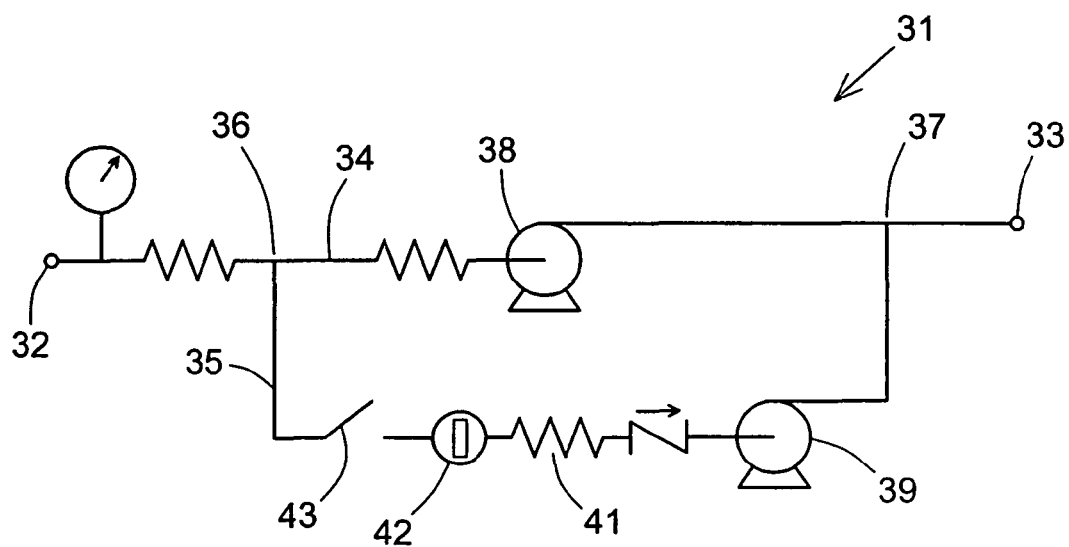
FIG. 2 is a diagram of the components of a second analytical device embodying the features of the present invention.

FIG. 2 represents a system 31 containing two pumps rather than a single pump, although still within the scope of the invention. Similar to the system 10 depicted in FIG. 1, exhaled breath enters the system 31 of FIG. 2 at a single inlet 32 and leaves at a single outlet 33, and the system divides into a main stream 34 and a side stream 35 at a dividing junction 36, the two streams recombining at a downstream junction 37. The first pump 38 is in the main stream 34 downstream of the junction 36 where the two streams are first formed, and the second pump 39 is in the side stream 35. The second pump 39 can compensate for variations in the flow resistance 41 through the side stream, particularly when the resistance is in the analyte sensor 42. The second pump 39 also permits independent flow rates to be established for the main stream 34 and the side stream 35. The independent flow rates can be configured by software or on a real-time basis, without exchanging the components. In the embodiment shown in FIG. 2, the second pump 39 is downstream from the analyte sensor 42 so that the pump effluent does not interfere with the signal emitted by the sensor 42.

Figure 3:
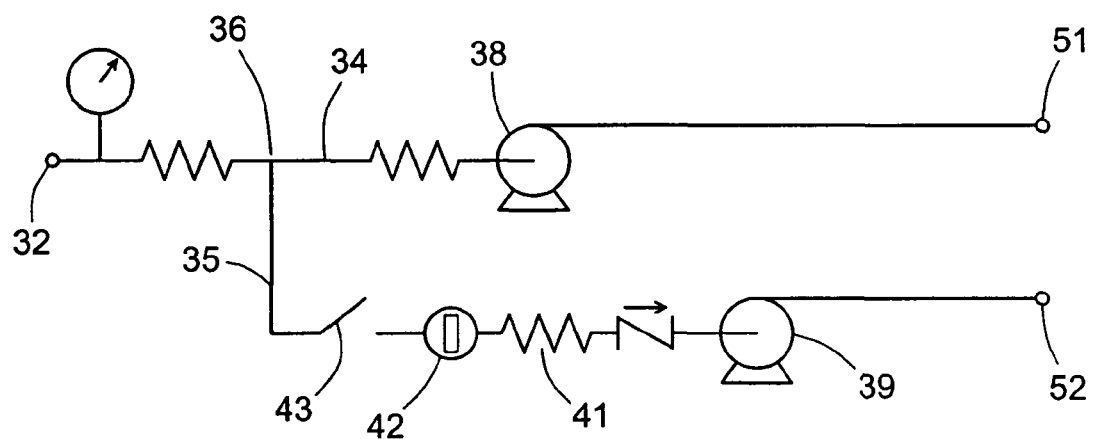
FIG. 3 is a diagram of the components of a third analytical device embodying the features of the present invention.

As in the single-pump embodiment of FIG. 1, the dual-pump system of FIG. 2 can utilize resistors that offer variable resistance as well as variable-speed pumps. A side stream valve 43 is shown in the dual-pump system. Alternatively, the side stream valve 43 can be eliminated by using the second pump 39 itself to open and close the side stream to flow. A further variation is shown in FIG. 3, where the junction 37 at which the main and side streams are recombined (FIG. 2) has been eliminated, and the main and side streams 34, 35 vent separately through separate outlets 51, 52, respectively.

The use of a side stream as shown in each of the Figures herein (element 17 of FIG. 1 and element 35 of FIGS. 2 and 3) offers various advantages. With the analyte sensor 21, 42 positioned in the side stream, the flow rate of exhaled breath passing through the analyte sensor can be reduced and a small analyte sensor, particularly one that responds quickly to the analyte due to its small size, can thereby be used. The flow rate through the side stream can thus be limited to a rate within a range of 5 cm$^3$/s to 11 cm$^3$/s, or in certain embodiments a range of 6 cm$^3$/s to 10 cm$^3$/s, or a range of 7 cm$^3$/s to 9 cm$^3$/s. This can be done while flow through the main stream occurs at a higher rate, such as for example 40 cm$^3$/s to 45 cm$^3$/s. Furthermore, a portion of the breath passing through the entire device can be retained in the region of the sensor for an extended contact time to incubate the sample and sensor prior to the measurement. A typical incubation time may be 1 minute. The sensor can then be removed for analysis or measurement. Incubation is of value for sensors that respond too slowly to produce a real-time analysis of a moving stream. Still further, the placement of the analyte sensor in a side stream allows the user to pass multiple cycles of breath across the sensor before flow through the device as a whole is stopped. For example, with a sensor that has a volume of 5.0 cm$^3$ and a side stream that accommodates a breath flow of 8.0 cm$^3$/s, leaving the side stream open for 3.0 seconds will cause 24.0 cm of breath to cross the sensor before the final 5.0 cm$^3$ is trapped in the side stream. Examples of periods of time during which the side stream is left open are periods of 1 to 10 seconds in duration, 1 to 7 seconds in duration, and 1 to 5 seconds in duration. This is useful for flushing the sensor prior to the analysis, thereby purging the sensor of extraneous gases with which the sensor was in contact prior to the analysis. The start of flow through the side stream can also be delayed for selected intervals following the start of the flow of exhaled breath through the device as a whole, for reasons of flushing or equilibration. In certain embodiments of the invention, for example, the opening of the side stream will be delayed for an interval of between 5 second and 9 seconds after the start of flow of exhaled breath through the device, and in certain other embodiments, the interval will be between 6 seconds and 8 seconds. The optimum interval for a child may differ from the optimum interval for an adult.

With the inclusion of the side stream shut-off valve, a separate side stream pump, or both, the side stream allows the system to be operated in a mode that can be termed a "stopped-flow operation." Stopping the flow allows the system to create a stable testing environment that can be maintained for a much longer period than is possible in a flowing system. As noted above, a one-minute static exposure time is illustrative, although much longer or shorter exposure times can be used as well.

The system and configurations described herein can be used for the analysis of many different analytes in exhaled breath, including gases that are present only in trace quantities, such as NO. For purposes of this specification and the appended claims, the expression "trace gas" denotes gases whose concentrations are below 1 part per million (on a volume basis), and preferably, depending on the significance of the analyte and the range within which variations can indicate a particular physiological condition or the onset of such a condition, below 300 parts per billion, below 200 parts per billion, or below 100 parts per billion. All concentrations herein, unless otherwise noted, are by volume. The invention is of particular interest in conjunction with a sensor consisting of cytochrome c in a sol-gel xerogel to measure NO. Sensors of this type and related technology are disclosed in the following pending U.S. patent applications, published U.S. patent applications, and issued U.S. patents: U.S. patent application Ser. No. 11/053,046, filed Feb. 7, 2005; U.S. patent application Ser. No. 11/053,253, filed Feb. 5, 2005; U.S. 2004-0017570 A1, published Jan. 29, 2004 (application Ser. No. 10/334,625, filed Dec. 30, 2002); U.S. 2005-0053549 A1, published Mar. 10, 2005 (application Ser. No. 10/659,408, filed Sep. 10, 2003); U.S. 2005-0083527 A1, published Apr. 21, 2005 (application Ser. No. 10/767,709, filed Jan. 28, 2004); U.S. Pat. No. 5,795,187, issued Aug. 18, 1998; and U.S. Pat. No. 6,010,459, issued Jan. 4, 2000. The disclosures of all patents and patent applications cited in this specification are hereby incorporated herein by reference.

The foregoing is offered primarily for purposes of illustration, and variations can be made without departing from the scope of the invention. The locations of the pumps, for example, can vary. When a single pump is used, the pump can be placed upstream of the juncture where the flow passage is divided into two streams, and when using either one pump or two, the pump(s) can be placed upstream of the sensor. Further variations and embodiments of the invention will be readily apparent to those skilled in the art.

What is claimed is:

1. A diagnostic apparatus for detecting an analyte in exhaled breath, said apparatus comprising:
    a housing having a flow-through passage and adapted to receive exhaled breath from a subject;
    an analyte sensing element responsive to said analyte when retained in said flow-through passage; and
    a pump means for moving said exhaled breath from a subject and through said flow-through passage at a controlled rate;
    wherein said flow-through passage comprises a primary passage and a secondary passage branched off from said primary passage;
    wherein said flow-through passage divides into said primary passage and said secondary passage at an upstream junction in said flow-through passage and said secondary passage recombines with said primary passage at a downstream junction in said flow-through passage; and wherein said pump means comprises a first pump in said primary passage and a second pump in said secondary passage.

2. The apparatus of claim 1 further comprising a pressure sensor arranged to detect the pressure of exhaled breath entering said primary flow-through passage.

3. The apparatus of claim 1 further comprising flow resistance means in said primary flow-through passage.

4. The apparatus of claim 3 wherein said flow resistance means is an orifice.

5. The apparatus of claim 3 wherein said flow resistance means is a variable flow resistor.

6. The apparatus of claim 1 wherein said primary and secondary flow-through passages are vented separately.

7. The apparatus of claim 1 further comprising a valve arranged to allow or prevent flow through said secondary flow-through passage.

8. The apparatus of claim 1 further comprising a check valve in said secondary flow-through passage.

9. The apparatus of claim 1 further comprising a first flow resistance means in said primary flow-through passage and a second flow resistance means in said secondary flow-through passage.

10. The apparatus of claim 9 wherein said first flow resistance means is a variable flow resistor.

11. The apparatus of claim 1 wherein said analyte sensing element is cytochrome c in a sol-gel matrix.

12. The apparatus of claim 1 wherein a concentration of the analyte to which the analyte sensing element is responsive is less than 1 part per million.

13. The apparatus of claim 1 wherein a concentration of the analyte to which the analyte sensing element is responsive is less than 100 parts per billion.

14. The apparatus of claim 1 wherein the analyte is nitric oxide (NO).

15. The diagnostic apparatus of claim 1, wherein the exhaled breath moved through the primary and secondary through passages is released to a surrounding atmosphere downstream of the recombination of the primary and secondary passages.

* * * * *